United States Patent [19]

Sun

[11] 4,045,912
[45] Sept. 6, 1977

[54] PRODUCTION OF ALFALFA SEEDS

[75] Inventor: Paul L. F. Sun, Beloit, Wis.

[73] Assignee: Kent Feeds, Inc., Muscatine, Iowa

[21] Appl. No.: 521,255

[22] Filed: Nov. 6, 1974

[51] Int. Cl.$^2$ ............................................. A01H 1/02
[52] U.S. Cl. ...................................................... 47/58
[58] Field of Search .............................. 47/58, DIG. 1

[56] References Cited

U.S. PATENT DOCUMENTS

| | | | |
|---|---|---|---|
| 3,570,181 | 3/1971 | Davis | 47/58 |
| 3,842,538 | 10/1974 | Barabas | 47/58 |

OTHER PUBLICATIONS

Probst, A. H. "Performance of Variety Blends in Soybeans", 1957, Agronomy Journal, vol. 49, pp. 148-150.
Reeve, P. A. and Sam C. Campbell, "Mixing Various Percentages of Male Parent Seed with Male Sterile Seed for Hybridization and the Subsequent Effect on the Productive Ability of Hybrids", 1954, Pro. Am. Soc. Sugar Beet, vol. 8, pp. 70-74.
Jackobs, J. A. and D. A. Miller, "Performance of Alfalfa (Medicago Sativah Blends Consisting of Long and Short Lived Varieties", Mar. 1973, Agronomy Journal, vol. 65, pp. 222-225.
"Effects of Vigor of Silines and Seeding Rates on Yield and Final Stand of an Alfalfa Two Clone Combination Admixed with Different Percentages of Si Seed", by Carnahan, H. L. and R. N. Faden, Jan. 1967, Crop Science, vol. 7, pp. 9-13.
Kehr, W. R. "Cross-Fertilization of Alfalfa as Affected by Genetic Markers, Planting Methods, Locations and Pollinator Species", May 1973, Crop Science, vol. 13, pp. 296-298.
Pepersen, M. W. and D. K. Barnes, "Alfalfa Seed Size as an Indicator of Hybridity", Jan. 1973, Crop Science, pp. 72-75.
Burton, Glenn W., "The Preformance of Various Mixtures of Hybrid and Parent Inbred Pearl Millet, Pennisetum Glaucum(L.)R.BR.", Journal of the American Society of Agronomy, 1948, vol. 40, pp. 908-915.
Hanson, C. H. et al., "The Relative Preformance of Alfalfa Varieties, Variety Crosses, and Variety Mixtures", Production Research Report, No. 83, 1964, U.S.D.A.
Breeding Field Crops by John Milton Poehlman, 1959, Published by: Holt, Rhinehart and Wilson, Inc., Chapter 13, pp. 255, 256, and Chapter 17 pp. 375, 376, Personal Property of Examiner Feyrer.
Introduction to Plant Breeding by F. N. Briggs and P. F. Knowles, Published by: Reinhold Books in Agricultural Science, 1967, Reinhold Publishing Corporation, Chapter 11, p. 137, Personal Property of Examiner Feyrer.

*Primary Examiner*—Edgar S. Burr
*Assistant Examiner*—James R. Feyrer
*Attorney, Agent, or Firm*—Neuman, Williams, Anderson & Olson

[57] ABSTRACT

Using controlled pollination a cytoplasmic male sterile alfalfa plant is crossed with a maintainer line to give cytoplasmic male sterile hybrid alfalfa seed which is recovered. Male sterile hybrid alfalfa plants derived from the said seed are then crossed, using random pollination, with male fertile alfalfa plants to give alfalfa seeds of good productivity.

17 Claims, No Drawings

PRODUCTION OF ALFALFA SEEDS

This invention relates to a method for the production of seed capable of growing alfalfa plants.

The greatest progress in the development of improved varieties of plants has come through the use of hybridization techniques whereby it has been possible to combine the best traits of one strain with other superior traits of a second strain to produce new strains possessing combinations of the superior traits of the parents. This is easier to accomplish with some species than with others. For example, corn can be hybridized quite readily due to the physical separation of the male and female reproductive parts of the plant. In some plants, the male and female elements are located on different plants.

The job of hybridizing alfalfa was not as easy to accomplish due to the fact that the male and female elements of alfalfa are normally present on the same plant, and are located within located within perfect flowers which contain both elements in a juxtaposed relationship. As a result of this arrangement, self-pollination as well as cross-pollination commonly occurs with the pollen being transmitted to a substantial degree by insects which visit many different alfalfa flowers. By utilization of methods to bring about the desired cross-pollination uniformly to the substantial exclusion of self-pollination or other undesired pollination, the essentially uniform production of seed capable of growing hybrid alfalfa is possible. For example, U.S. Pat. No. 3,570,181 describes a process for producing seed capable of growing hybrid alfalfa plants.

However, it has been found that hybrid alfalfa strains possess reduced seed producing ability to the extent that seed yield of male steriles has been found to be 50 % less than that of the pollinizer strain.

A considerable number of commercial alfalfa varieties currently marketed are progenies from open-pollinated seed or mixtures of inbreds or hybrids, within them, and are designated as "synthetics".

A serious disadvantage of the synthetic varieties certified seed is the reduction of both forage and seed productivity from an early generation (Syn 1) to the advanced generations (Syn 3 to Syn 5). In the synthetic 0 (parent) population there are few individuals while in successive generations there are many individuals due to the expanding population. Most certified synthetic seeds are in the synthetic 3, synthetic 4 or synthetic 5 generations, which generations involve considerable inbreeding by virtue of relatives mating. The most significant decline in forage productivity is found to come between the synthetic 1 and synthetic 2 generations.

The commercial production of seeds for growing alfalfa plants basically involves three stages, namely the production of breeder seeds, foundation seeds, and certified seeds. This is true in the case of either synthetic variety seeds or hybrid variety seeds. Breeder seed is the initial increase of seed of the strain which is developed by the breeder and from which foundation seed is derived. Foundation seed is the second generation of seed increase and from which certified seed is derived. Foundation seed has descended from a selection of recorded origin, under the direct control of the originator, a delegated representative, or a state or federal experimental station. Certified seeds are seeds for use in commercial crop production, produced from foundation, registered or certified seed. Certified seed is usually grown, processed and labeled under supervision and regulation of a public agency. Registered seed normally is distributed by growers or seedmen as planting stock for the production of certified seed.

One object of the invention is to provide a commercially practical process for the production of alfalfa seed possessing the forage production capability of hybrids.

Another object is to reduce the inbreeding that develops in advanced generations of synthetic varieties.

A further object of the invention is to provide methods for increasing the seed productivity of synthetic and hybrid variety alfalfa plants.

A still further object is to provide improvements in ease of planting and harvesting certified seed.

In general, the process of the present invention involves:

STEP 1

Crossing by controlled pollination a cytoplasmic male sterile alfalfa plant with a maintainer line to give cytoplasmic male sterile hybrid alfalfa seed and recovering said seed.

STEP 2

Crossing, using random pollination, the cytoplasmic male sterile hybrid alfalfa plants derived from the seed produced in Step 1 with male fertile alfalfa plants to give alfalfa seeds of good productivity.

STEP 3

Recovering the seeds of Step 2.

The seeds recovered by the foregoing steps are certified seeds which are adapted for use in commercial crop production. Intermediate Step 1 and Step 2 there may be various alfalfa plant crossings to produce breeder and foundation seeds using either controlled or random pollination.

The production and recovery of cytoplasmic male sterile alfalfa plants is described in U.S. Pat. No. 3,570,181. The male fertile alfalfa plant can be (a) a maintainer line; (b) the result of crossing a genic male sterile with a male fertile plant; (c) the result of crossing a cytoplasmic male sterile and a restorer line; or (d) a variety.

In the first step of the present process controlled pollination is practiced. Pollen transfer from the maintainer line to the cytoplasmic male sterile plant can be accomplished by pollen-carrying insects such as bees. Since the cytoplasmic male sterile plant is incapable of producing pollen, the pollination thereof is accomplished exclusively by pollen from the pollinizer plant in isolated condition. This controlled crossing or pollination produces seeds from which are produced cytoplasmic male sterile hybrid alfalfa plants. These male sterile hybrid alfalfa plants are subsequently crossed to give certified seeds of exceptional quality. Optionally, in this first step a cytoplasmic male sterile or genic male sterile plant can also be crossed under controlled pollination conditions with a restorer or common alfalfa plant to give a male fertile hybrid alfalfa plant which can be used subsequently for crossing under random conditions with the cytoplasmic male sterile hybrid plant which in all cases is produced in the first step of the process. The male sterile plants and the maintainer plants may be grown in alternating rows. A group of up to 2-3 adjoining rows of cytoplasmic male sterile plants may be effectively alternated with a group of up to 2-3 adjoining rows of the pollinizer plant. Such an arrangement makes possible a more efficient seed recovery using larger equipment. Once seed has formed upon the seed parents (male sterile line), it may be selectively recovered or harvested by combines or hand harvested for subsequent threshing by use of a plot thresher.

In the last step of the process, which produces the certified seed, random pollination must be practiced. Random crossing or pollination can be accomplished by random disturbtion of all genetic lines (male sterile hybrid plants and male fertile alfalfa plants) in the field and subjecting them to bee pollination. Seed is bulked together in harvesting by a combine.

For maximum seed production the ratio of male sterile hybrid alfalfa plants to male fertile plants in Step 2 must be in the range of 1:1 to 3:1. The data in Examples 1 and 2. illustrate this.

EXAMPLE 1

1. Materials:

Four male sterile lines, $T_1$-568ms × B46-37, $T_8$-54ms × B46-37, $T_9$-53 ms × B46-37 and $T_8$-54ms × B59 were selected as female parents. Three synthetic varieties, Kanza, Klondike and Superstan: two hybrids, $T_8$-54ms × MS-IW and $T_8$-54ms × VC51 and one inbred, B59, were selected as male parents (pollinizers).

2. Methods:
   A. Field Design
   a. Male and Female in Separate Rows

```
x x . o o
x x . o o
x x . o o
x x . o o
x x . o o
x x . o o
x x . o o
x x . o o
x x . o o
x x . o o
x x . o o
x x . o o
```

Each crossing block consists of two female rows and two male rows with one skip row between them. There were 12 plants in a row, and plants were space transplanted at 20-inch intervals. Row width was 40 inches. The inner row of male plants was 80 inches apart from the inner row of female plants and 120 inches from the outer row of female plants.

b. Male and Female Mixed Together

| 3 female / 1 male | 2 female / 1 male | 1 female / 1 male |
|---|---|---|
| x o x o | x o x o | x o x o |
| o o o o | o o o o | o x o x |
| o o o o | o x o x | x o x o |
| o x o x | x o x o | o x o x |
| x o x o | o o o o | x o x o |
| o o o o | o x o x | o x o x |
| o o o o | x o x o | x o x o |
| o x o x | o o o o | o x o x |
| x o x o | o x o x | x o x o |
| o o o o | x o x o | o x o x |
| o o o o | o o o o | x o x o |
| o x o x | o x o x | o x o x | male plant = x
female plant = o

There were four rows in each crossing block. Each row was 20 feet long with 40 inch row width. Male and female plants were mixed using the designed ratios. Seeds were germinated in the greenhouse and later space transplanted to the field at 20-inch intervals. Each crossing block was considered as a unit in the planting scheme. Blocks were 20 feet apart. The results are shown in Table I.

TABLE I

Seed yield response of male sterile lines to different planting patterns, and to different male to female ratios.

| Pedigree | Planting Pattern | Female Rows | Female to Male Ratio Designed | Actual | % of Male |
|---|---|---|---|---|---|
| $T_1$-568ms × B46-37 | (F) | Separate | outside | | 45.4 |
| $T_1$-568ms × B46-37 | (F) | | inside | | 56.0 |
| Klondike | (M) | | | | 100.0 |
| $T_1$-568ms × B46-37 | | Mixed | | 3 : 1 | 3 : 1 | 61.6 |
| Klondike | | | | | | 100.0 |
| $T_1$-568ms × B46-37 | | Mixed | | 1 : 1 | 0.7 : 1 | 78.7 |
| Klondike | | | | | | 100.0 |
| $T_8$-54ms × B46-37 | (F) | Separate | outside | | 36.1 |
| $T_8$-54ms × B46-37 | (F) | | inside | | 49.4 |
| Superstan | (M) | | | | 100.0 |
| $T_8$-54ms × B46-37 | | Mixed | | 3 : 1 | 3.2 : 1 | 65.1 |
| Superstan | | | | | | 100.0 |
| $T_8$-54ms × B46-37 | | Mixed | | 1 : 1 | 1.1 : 1 | 92.3 |
| Superstan | | | | | | 100.0 |
| $T_8$-54ms × B59 | (F) | Separate | outside | | 78.7 |
| $T_8$-54ms × B59 | (F) | | inside | | 112.3 |
| Kanza | (M) | | | | 100.0 |
| $T_8$-54ms × B59 | | Mixed | | 3 : 1 | 2.5 : 1 | 97.8 |
| Kanza | | | | | | 100.0 |
| $T_8$-54ms × B59 | | Mixed | | 1 : 1 | 1 : 1 | 141.0 |
| Kanza | | | | | | 100.0 |
| $T_1$-568ms × B46-37 | (F) | Separate | outside | | 51.6 |
| $T_1$-568ms × B46-37 | (F) | | inside | | 74.5 |
| $T_8$-54ms × MS-IW | (M) | | | | 100.0 |
| $T_1$-568ms × B46-37 | | Mixed | | 3 : 1 | 3 : 1 | 115.1 |
| $T_8$-54ms × MS-IW | | | | | | 100.0 |
| $T_1$-568ms × B46-37 | | Mixed | | 1 : 1 | 0.8 : 1 | 101.4 |
| $T_8$-54ms × MS-IW | | | | | | 100.0 |
| $T_9$-53ms × B46-37 | (F) | Separate | outside | | 47.0 |
| $T_9$-53ms × B46-37 | (F) | | inside | | 87.3 |
| $T_8$-54ms × VC51 | (M) | | | | 100.0 |
| $T_9$-53ms × B46-37 | | Mixed | | 3 : 1 | 2.3 : 1 | 86.8 |
| $T_8$-54ms × VC51 | | | | | | 100.0 |
| $T_9$-53ms × B46-37 | | Mixed | | 3 : 1 | 3 : 1 | 100.0 |
| $T_8$-54ms × VC51 | | | | | | 100.0 |
| $T_9$-53ms × B46- | (F) | Separate | outside | | 33.4 |
| $T_9$-53ms × B46-37 | (F) | | inside | | 49.3 |

TABLE I-continued

Seed yield response of male sterile lines to different planting patterns, and to different male to female ratios.

| Pedigree | Planting Pattern | Female Rows | Female to Male Ratio Designed | Actual | % of Male |
|---|---|---|---|---|---|
| D59 | (M) | | | | 100.0 |

EXAMPLE 2

1. Materials:

The medium seed yield male sterile line $T_1$-567ms-43, was selected as female parent, and medium-high seed yield line, B46-37, and low seed yield line VC-51-17, were selected as male parents.

2. Methods:

Male and female plants were mixed in 3 different ratios. They are as follows:

| Mixing Ratio | Female | | Male |
|---|---|---|---|
| 1 | 3 | : | 1 |
| 2 | 2 | : | 1 |
| 3 | 1 | : | 1 |

Split plot design with 3 mixing ratios, 2 pollinizers and 2 replications were used. Field layout was the same as seed production experiment 1.

All the plants were established by vegetative cuttings from the designed clones. Both leaf cutter bees and honey bees were used for pollination. Some plants in the crossing blocks were damaged by gophers. This caused the deviation on original designed male to female ratio. The results are shown in Table II.

TABLE II

Seed yield response of male sterile lines to different males (pollinizers) and different male to female ratios

| Treatment | | Replicate I | | | | Replicate II | | | | Average of 2 Replicates | |
|---|---|---|---|---|---|---|---|---|---|---|---|
| Strain* | Design Ratio | # Plants | Total Gm. | Wt./Pl. Gm. | % Hybrid | # Plants | Total Gm. | Wt./Pl. Gm. | % Hybrid | % Hybrid | Wt./Pl. |
| Female | 3 | 36 | 1496 | 41.6 | 73.3 | 36 | 1300 | 36.1 | 76.3 | 74.8 | 38.9 |
| Male 1 | 1 | 12 | 544 | 45.3 | | 12 | 403 | 33.6 | | 74.8 | |
| Female | 2 | 30 | 1458 | 48.6 | 69.6 | 32 | 1552 | 48.5 | 74.8 | 72.2 | 48.6 |
| Male 1 | 1 | 16 | 676 | 42.3 | | 16 | 520 | 32.5 | | | |
| Female | 1 | 24 | 1589 | 66.2 | 59.4 | 24 | 1284 | 53.5 | 54.3 | 56.9 | 59.9 |
| Male 1 | 1 | 24 | 1088 | 45.3 | | 21 | 944 | 45.0 | | 58.5 | |
| Female (No Male) | | 48 | 813 | 16.9 | | 47 | 1018 | 21.7 | | | |
| Male (No Fem) | | 37 | 1512 | 40.9 | | 44 | 2185 | 48.9 | | | |
| Female | 3 | 36 | 525 | 14.6 | 74.8 | 34 | 412 | 12.1 | 85.0 | 79.9 | 13.4 |
| Male 2 | 1 | 10 | 147 | 14.7 | | 10 | 64 | 6.4 | | 82.3 | |
| Female | 2 | 32 | 554 | 17.3 | 68.2 | 32 | 420 | 13.3 | 78.0 | 73.1 | 15.3 |
| Male 2 | 1 | 14 | 225 | 16.1 | | 8 | 60 | 7.5 | | 79.6 | |
| Female | 1 | 24 | 600 | 25.0 | 60.9 | 17 | 224 | 13.2 | 57.6 | 59.3 | 19.1 |
| Male 2 | 1 | 21 | 336 | 16.0 | | 13 | 126 | 9.7 | | 64.1 | |
| Female (No Male) | | 48 | 420 | 8.8 | | 48 | 384 | 8.0 | | | |
| Male (No Fem) | | 46 | 840 | 18.3 | | 31 | 340 | 11.0 | | | |

*Female: $T_1$ - 567 ms (Average in seed set)
Male 1: B46 -37 (High seed set)
Male 2: VC51 -17 (Low seed set)

cl EXAMPLE 3

This example illustrates the process of the present invention with four parental lines and alfalfa plants of specific combining ability.

| Generation | 0 | A + B + C + D | |
|---|---|---|---|
| | 1 | (A × B) (C × D) | (Breeder Seed) |
| | 2 | (A B) (C D) | (Certified Seed) |
| Where: | | A = Cytoplasmic male sterile line | |
| | | B = Maintainer Line | |
| | | C = Cytoplasmic or genic male sterile line | |
| | | D = Restorer line or normal line | |
| | | A × B → $F_1$ (A B) male sterile | |
| | | C × D → $F_1$ (C D) normal (both male and female are functioning) | |

| Processing: | 1. | Controlled crosses in generation 1, that is, no selfing allowed. |
|---|---|---|
| | 2. | Random pollination in generation 2 with some selfing and full sibbing in cross (C × D). |
| | 3. | (A B) : (C D) = 3 : 1 or 2 : 1 or 1 : 1 |

EXAMPLE 4

This example illustrates the process of the invention with six parental lines and alfalfa plants of specific combining ability.

| Generation | 0 | A + B + C + D + E + F | |
|---|---|---|---|
| | 1 | (A × B) (C × D) (E × F) | (Breeder Seed) |
| | 2 | (A B) (C D) (E F) | (Certified Seed) |
| Where: | | A = Cytoplasmic male sterile line | |
| | | B = Maintainer line | |
| | | C = Cytoplasmic or genic male sterile line | |
| | | D = Restorer line or normal line | |
| | | E = Cytoplasmic or genic male sterile line | |
| | | F = Restorer line or normal line | |
| | | A × B → $F_1$ (A B) male sterile | |
| | | C × D → $F_1$ (C D) normal | |
| | | E × F → $F_1$ (E F) normal | |
| Processing: | 1. | Controlled crosses in generation 1, that is, no selfing allowed. | |
| | 2. | Random pollination in generation 2 with some selfing. | |
| | 3. | Selfing and full sibbing within the 2 single crosses, (C × D), (E × F) and crossing among the 3 single crosses are expected to occur. | |
| | 4. | (AB) : (CD) : (EF) = 6 : 1 : 1 or = 4 : 1 : 1 or = 2 : 1 : 1 or = etc. | |

EXAMPLE 15

This example illustrates the invention where controlled pollination is practiced in generations 1 and 2 with random pollution in generation 3 from which the certified seeds are obtained. Alfalfa plants of specific combining ability are employed.

| Generation | 0 | $A + B_1 + B_2 + C + D_1 + D_2$ | |
|---|---|---|---|
| | 1 | $(A \times B_1)$ and $(C \times D_1)$ | (Breeder Seed) |
| | 2 | $(AB_1 \times B_2)$ and $(CD_1 \times D_2)$ | (Foundation Seed) |
| | 3 | $(AB_1 B_2) (CD_1 D_2)$ | (Certified Seed) |
| Where: | A | = Cytoplasmic male sterile line | |
| | $B_1$ | = Maintainer line | |
| | $B_2$ | = Maintainer line | |
| | C | = Cytoplasmic male sterile line | |
| | $D_1$ | = Maintainer line | |
| | $D_2$ | = Restorer line | |
| Processing: | 1. | Controlled crosses in generation 1 and 2, that is, no selfing allowed. | |
| | 2. | Random pollination in generation 3 with some selfing and full sibbing in cross $(CD_1 \times D_2)$. | |
| | 3. | $(AB_1 B_2) : (CD_1 D_2) = 3 : 1$ or $2 : 1$ or $1 : 1$. | |

EXAMPLE 6

This example illustrates the processes of the invention with eight parallel lines and alfalfa plants of general combining ability.

| Generation | 0 | $A + B + C + D + E + F + G + H$ | |
|---|---|---|---|
| | 1 | $(A \times B)(C \times D)(E \times F)(G \times H)$ | (Breeder Seed) |
| | 2 | $(A B)(C D), (E F)(G H)$ | (Foundation Seed) |
| | 3 | $(A B C D)(E F G H)$ | (Certified Seed) |
| Where: | A | = Cytoplasmic male sterile line | |
| | B | = Maintainer line | |
| | C | = Cytoplasmic male sterile line or genic male sterile line | |
| | D | = Restorer (or partial restorer) or maintainer line or normal line | |
| | E | = Cytoplasmic male sterile line | |
| | F | = Maintainer line (or partial maintainer line) | |
| | G | = Cytoplasmic male sterile line or genic male sterile line | |
| | H | = Restorer line | |
| Processing: | 1. | Controlled crosses in generation 1, that is, no selfing allowed. | |
| | 2. | Controlled or random pollination in generation 2. | |
| | 3. | Random pollination in generation 3. | |
| | 4. | When random pollination practiced in generation 2 $AB : CD = 3 : 1$ or $2 : 1$ $EF : GH = 3 : 1$ or $2 : 1$ | |
| | 5. | $(A B C D) : (E F G H) = 1 : 1$ | |

Examples 7 through 11 illustrate the use of the invention with locally adapted lines for the production of seed for local adaptation.

EXAMPLE 7

This example illustrates the invention with single maintainer and locally adapted alfalfa plants.

| Generation | 0 | $A + B + LAL$ | |
|---|---|---|---|
| | 1 | $A \times B$ | (Breeder Seed) |
| | 2 | $A B \times LAL$ | (Certified Seed) |
| Where: | A | = Cytoplasmic male sterile line | |
| | B | = Maintainer line | |
| | | $A \times B = F_1 (A B)$ male sterile | |
| | LAL | = Locally adapted line (lines, variety) | |
| Processing: | 1. | Controlled cross in generation 1, that is, no selfing allowed. | |
| | 2. | Random pollination in generation 2. | |
| | 3. | $AB : LAL = 3 : 1$ or $2 : 1$ or $1 : 1$. | |

EXAMPLE 8

This example is illustrative of the use of two locally adapted lines.

| Generation | 0 | $A + B + LAL 1 + LAL 2$ | |
|---|---|---|---|
| | 1 | $A \times B$ | (Breeder Seed) |
| | 2 | $AB \times LAL 1 \times LAL 2$ | (Certified Seed) |
| Where: | A | = Cytoplasmic male sterile | |
| | B | = Maintainer line | |
| | | $A \times B = F_1 (A B)$ male sterile | |
| | LAL 1 | = Locally adapted line 1 (variety) | |
| | LAL 2 | = Locally adapted line 2 (or variety) | |
| Processing: | 1. | Controlled cross in generation 1, that is, no selfing allowed. | |
| | 2. | Random pollination in generation 2. | |
| | 3. | $AB : LAL 1 : LAL 2 = 6 : 1 : 1$ or $= 4 : 1 : 1$ or $= 2 : 1 : 1$. | |

EXAMPLE 9

This example illustrates the use of two differnt maintainer lines.

| Generation | 0 | $A + B_1 + B_2 + LAL$ | |
|---|---|---|---|
| | 1 | $A \times B_1$ | (Breeder Seed) |
| | 2 | $AB_1 \times B_2$ | (Foundation Seed) |
| | 3 | $(AB_1 B_2) (LAL)$ | (Certified Seed) |
| Where: | A | = Cytoplasmic male sterile line | |
| | $B_1$ | = Maintainer line | |
| | $B_2$ | = Maintaner line | |
| | LAL | = Locally adapted line (variety) | |
| Processing: | 1. | Controlled cross in generation 1 and 2, that is, no selfing allowed. | |
| | 2. | Random pollination in generation 3. | |
| | 3. | $AB_1 B_2 : LAL = 3 : 1$ or $2 : 1$ or $1 : 1$. | |

EXAMPLE 10

This example illustrates the use of two maintainer lines and two locally adapted lines.

| Generation | 0 | $(A + B + LAL 1 + C + D + LAL 2)$ | |
|---|---|---|---|
| | 1 | $A \times B$ and $C \times D$ | (Breeder Seed) |
| | 2 | $AB \times LAL 1$ and $CD \times LAL 2$ | (Foundation Seed) |
| | 3 | $(AB LAL 1) (CD LAL 2)$ | (Certified Seed) |
| Where: | A | = Cytoplasmic male sterile line | |
| | B | = Maintainer line | |
| | LAL 1 | = Locally adapted line (or variety) | |
| | | $A \times B = F_1 (A B)$ male sterile | |
| | C | = Cytoplasmic male sterile line | |
| | D | = Maintainer line | |
| | | $C \times D = F_1 (C D)$ male sterile | |
| | LAL 2 | = Locally adapted line | |
| Processing: | 1. | Controlled cross in generation 1, that is, no selfing allowed. | |
| | 2. | Controlled or random pollination in generation 2. | |
| | 3. | Random pollination in generation 3. | |
| | 4. | If random pollination practiced $AB : LAL 1 = 3 : 1$ or $2 : 1$ $CD : LAL 2 = 3 : 1$ or $2 : 1$ | |
| | 5. | $AB LAL 1 : CD LAL 2 = 1 : 1$. | |

EXAMPLE 11

This example illustrates the use of four maintainer lines and two locally adapted lines.

| Generation | 0 | $A + B_1 + B_2 + LAL 1 + C + D_1 + D_2 + LAL 2$ | |
|---|---|---|---|
| | 1 | $(A \times B_1)$ and $(C \times D_1)$ | (Breeder Seed) |
| | 2 | $(AB_1 \times B_2)$ and $(CD_1 \times D_2)$ | (Foundation Seed 1) |
| | 3 | $(AB_1 B_2 \times LAL 1)$ and | (Foundation |

|   |   |   |   |
|---|---|---|---|
| 4 | $(AB_1 B_2 LAL 1)$ $(CD_1 D_2 LAL 2)$ | $(CD_1 D_2 LAL 2)$ | Seed 2) (Certified Seed) |

Where:
A = Cytoplasmic male sterile line
$B_1$ = Maintainer line
$B_2$ = Maintainer line
LAL 1 = Locally adapted line (variety)
C = Cytoplasmic male sterile line
$D_1$ = Maintainer line
$D_2$ = Maintainer line
LAL 2 = Locally adapted line (variety)
$A \times B_1 = F_1 (AB_1)$ male sterile
$AB_1 \times B_1 = F_1 (AB_1 B_2)$ male sterile
$C \times D_1 = F_1 (CD_1)$ male sterile
$CD_1 \times D_2 = F_1 (CD_1 D_2)$ male sterile Processing:
1. Controlled cross in generation 1, that is, no selfing allowed.
2. Controlled cross in generation 2.
3. Controlled or random pollination in generation 3.
4. Random pollination in generation 4.
5. If random pollination practiced in generation 3
   $AB_1 B_2$ : LAL 1 = 3 : 1 or 2 : 1
   $CD_1 D_2$ : LAL 2 = 3 : 1 or 2 : 1
6. $AB_1 B_2$ LAL 1 : $CD_1 D_2$ LAL 2 = 1 : 1

Since male sterile lines are used as one of the major integral parts of the present process, it is somewhat difficult to compare it and synthetics on the same genetic ground. Nevertheless, field trials were carried out to compare forage and seed productivity of synthetic alfalfa seeds, hybrid alfalfa seeds and alfalfa seeds produced according to the present invention. The results of the field trials are tabulated in Tables III and IV.

TABLE III

Forage and seed productivity of different breeding processes, Present Process, Hybrid and synthetic varieties in several tests.

| Test | Breeding Process | Genetic Constitution | Product | Forage Yield* | Seed Yield Grams/Plot |
|---|---|---|---|---|---|
| (1) | Present Process | $(A_1 \times B_1) \times (A_2 \times R_1)$ | $F_1 - A_1 B_1 A_2 R_1 +$ $F_2 - A_2 R_1 +$ Sib - $A_2 R_1$ | 106 | 482 |
|  | Hybrid | " | $F_1 - A_1 B_1 A_2 R_1$ | 106 | 196 |
|  | Present Process | $A_3 \times B_1 \times (A_2 \times R_1)$ | $F_1 - A_3 B_1 A_2 R_1 +$ $F_2 - A_2 R_1 +$ Sib - $A_2 R_1$ | 106 | 560 |
|  | Hybrid | " | $F_1 - A_3 B_1 A_2 R_1$ | 107 | 174 |
|  | Synthetic | Superstan | — | 100 |  |
| (2) | Present Process | $(A_4 \times B_2) \times (A_2 \times R_1)$ | $F_1 - A_4 B_2 A_2 R_1 +$ $F_2 - A_2 R_1 +$ Sib - $A_2 R_1$ | 104 | 570 |
|  | Hybrid | " | $F_1 - A_4 B_2 A_2 R_1$ | 111 | 146 |
|  | Present Process | $(A_5 \times B_3) \times (A_2 \times R_1)$ | $F_1 - A_5 B_3 A_2 R_1 +$ $F_2 - A_2 R_1 +$ Sib - $A_2 R_1$ | 114 | 290 |
|  | Hybrid | " | $F_1 - A_5 B_3 A_2 R_1$ | 116 | 48 |
|  | Synthetic | Vernel | — | 100 |  |
| (3) | Present Process | $(A_6 \times B_2) \times (A_1 \times R_1)$ | $F_1 - A_6 B_2 A_1 R_1 +$ $F_2 - A_1 R_1 +$ Sib - $A_1 R_1$ | 106 | 370 |
|  | Hybrid | " | $F_1 - A_6 B_4 A_1 R_1$ | 100 | 152 |
|  | Present Process | $(A_7 \times B_4) \times (A_8 \times R_1)$ | $F_1 - A_7 B_4 A_8 R_1 +$ $F_2 - A_8 R_1 +$ Sib - $A_8 R_1$ | 101 | 320 |
|  | Hybrid | " | $F_1 - A_7 B_4 A_8 R_1$ | 101 | 126 |
|  | Synthetic | Saranac | — | 100 |  |
| (4) | Present Process | $A_5 \times B_5 \times A_3 \times R_1$ | $F_1 - A_5 B_5 A_3 R_1 +$ $F_2 - A_3 R_1 +$ Sib - $A_3 R_1$ | 105 | 240 |
|  | Hybrid | " | $F_1 - A_5 B_5 A_3 R_1$ | 106 | 70 |
|  | Synthetic | Vernel | — | 100 |  |
| (5) | Present Process | $(A_1 \times B_1) \times (A_2 \times R_1)$ | $F_1 - A_1 B_1 A_2 R_1 +$ $F_2 - A_2 R_1 +$ Sib - $A_2 R_1$ | 106 | 482 |
|  | Hybrid | " | $F_1 - A_1 B_1 A_2 R_1$ | 111 | 196 |
| (5) | Present Process | $(A_3 \times B_1) \times (A_2 \times R_1)$ | $F_1 - A_3 B_1 A_2 R_1 +$ $F_2 - A_2 R_1 +$ Sib - $A_2 R_1$ | 109 | 560 |
|  | Hybrid | " | $F_1 - A_3 B_1 A_2 R_1$ | 109 | 174 |
|  | Present Process | $(A_4 \times B_2) \times (A_2 \times R_1)$ | $F_1 - A_4 B_2 A_2 R_1 +$ $F_2 - A_2 R_1 +$ Sib - $A_2 R_1$ | 113 | 570 |
|  | Hybrid | " | $F_1 - A_4 B_2 A_2 R_1$ | 105 | 146 |
|  | Present Process | $(A_6 \times B_2) \times (A_1 \times R_1)$ | $F_1 - A_6 B_2 A_1 R_1 +$ $F_2 - A_1 R_1 +$ Sib - $A_1 R_1$ | 108 | 370 |
|  | Hybrid | " | $F_1 - A_6 B_2 A_1 R_1$ | 105 | 152 |
|  | Synthetic | Vernel | — | 100 |  |
| Average | (Present Process |  |  | 107 | 438 |
|  | (Hybrid |  |  | 107 | 143 |
|  | (Synthetic |  |  | 100 |  |

*Forage yield is percent of synthetic set at 100

TABLE IV

Comparison of seed productivity of alfalfa seeds produced by the present invention versus synthetic varieties of alfalfa seeds.

| Breeding Systems | Genetic Constitution | Product | Seed Yield (grams/plot) |
|---|---|---|---|
| Present Process 1 | $A_1 \times B_1 \times$ Saranac | $F_1 - A_1 B_1$ Saranac + | 430 |

TABLE IV-continued

Comparison of seed productivity of alfalfa seeds produced by the present invention versus synthetic varieties of alfalfa seeds.

| Breeding Systems | Genetic Constitution | Product | Seed Yield (grams/plot) |
|---|---|---|---|
| 2 | $A_3 \times B_1 \times$ Saranac | $F_1$ - $A_3 B_1$ Saranac + Saranac | 635 |
| 3 | $A_4 \times B_2 \times$ Saranac | $F_1$ - $A_4 B_2$ Saranac + Saranac | 890 |
| 4 | $A_6 \times B_2 \times$ Saranac | $F_1$ - $A_6 B_2$ Saranac + Saranac | 976 |
| 5 | $A_9 \times B_1 \times$ Saranac | $F_1$ - $A_9 B_1$ Saranac + Saranac | 560 |
| 6 | $A_3 \times B_1 \times$ ML-1W | $F_1$ - $A_3 B_1$ ML-1W + ML-1W | 660 |
| 7 | $A_9 \times B_1 \times$ ML-1W | $F_1$ - $A_9 B_1$ ML-1W + ML-1W | 462 |
| 8 | $A_9 \times B_1 \times$ Yellow | $F_1$ - $A_9 B_1$ Yellow + Yellow | 920 |
| Mean | | | (692 grams) |
| Synthetic 1 | Cayuga × Saranac | | 625 |
| 2 | Cherokee × Saranac | | 455 |
| 3 | Dawson × Saranac | | 570 |
| 4 | Kanza × Saranac | | 260 |
| 5 | I D × Saranac | | 414 |
| 6 | Klondike | | 526 |
| 7 | K D A | | 250 |
| Mean | | | (443 grams) |

The data presented in Tables III and IV show that the mean forage productivity of alfalfa seeds produced by the present invention was equal to hybrid seeds and 7% greater than synthetic alfalfa seeds. This is a very significant increase. The seed productivity of alfalfa plants produced in accordance with this invention was about 3-fold that of hybrid plants (438 vs. 143 grams per plot) and was about 50% greater than synthetic alfalfa plants (692 vs. 443 grams per plot).

Those modifications and equivalents which fall within the spirit of the invention are to be considered a part thereof.

What is claimed is:

1. A process for producing alfalfa seeds which comprises:
   Step A - crossing by controlled pollination cytoplasmic male sterile alfalfa plants with maintainer line alfalfa plants to give cytoplasmic male sterile hybrid alfalfa seeds,
   Step B - selectively recovering the hybrid seeds produced in Step A,
   Step C - crossing, using random pollination, cytoplasmic male sterile hybrid alfalfa plants derived from seed produced in Step A randomly mixed with male fertile alfalfa plants to give alfalfa seeds, the ratio of male sterile hybrid alfalfa plants to male fertile alfalfa plants being in the range of about 1:1 to 3:1, and
   Step D - non-selectively recovering the seeds from the last-mentioned crossing.

2. A process for producing alfalfa seeds which comprises:
   Step A - crossing by controlled pollination,
   1. cytoplasmic male sterile alfalfa plants with maintainer line alfalfa plants to give cytoplasmic male sterile hybrid alfalfa seeds, and
   2. cytoplasmic male sterile alfalfa plants with restorer line alfalfa plants to give male fertile hybrid alfalfa seeds,
   Step B - selectively recovering the hybrid seeds from both the crossings of Step A(1) and Step A(2),
   Step C - crossing, using random pollination, the hybrid alfalfa plants derived from randomly mixing and planting the seeds produced in Step A(1) and Step A(2) to give alfalfa seeds, the ratio of male sterile hybrid alfalfa plants to male fertile alfalfa plants being in the range of about 1:1 to 3:1, and
   Step D - non-selectively recovering the seeds from the last-mentioned crossing.

3. The process of claim 2 in which the cross in Step A(2) is
   1. between a cytoplasmic male sterile line of alfalfa plants and a restorer line of alfalfa plants, and
   2. between a second cytoplasmic male sterile line of alfalfa plants and a second restorer line of alfalfa plants,
   and the Step C crossing is between plants from the seeds produced in Step A(1) and the seeds produced in A(2) (1) and A(2) (2).

4. A process for producing alfalfa seeds which comprises:
   Step A - crossing by controlled pollination,
   1. cytoplasmic male sterile alfalfa plants with maintainer line alfalfa plants to give cytoplasmic male sterile hybrid alfalfa seeds, and
   2. 1. genic male sterile alfalfa plants with normal line alfalfa plants to give male fertile hybrid alfalfa seeds,
   2. 2. a second genic male sterile line of alfalfa plants and a second normal line of alfalfa plants to give male fertile hybrid alfalfa seeds, and
   Step B - selectively recovering the hybrid seeds from the crossings of Step A(1) and Step A(2) (1) and Step A(2) (2),
   Step C - crossing, using random pollination, the cytoplasmic male sterile hybrid alfalfa plants derived from the seeds produced in Step A(1) randomly mixed with plants derived from seeds produced in Step A(2) (1) and Step A(2) (2) to give alfalfa seeds, the ratio of male sterile hybrid alfalfa plants to male fertile alfalfa plants being in the range of about 1:1 to 3:1, and
   Step D - non-selectively recovering the seeds from the last-mentioned crossing.

5. A process for producing alfalfa seeds which comprises:
   Step A - crossing by controlled pollination, 1. a cytoplasmic male sterile line of alfalfa plants with a maintainer line of alfalfa plants to give cytoplasmic male sterile hybrid alfalfa seeds, and
2. a genic male sterile line of alfalfa plants with a normal line of alfalfa plants to give male fertile hybrid alfalfa seeds, Step B - selectively recovering the hybrid seeds from both the crossings of Step A(1) and Step A(2), Step C - crossing, using random pollination, the hybrid alfalfa plants derived from randomly mixing and planting the seeds produced in Step A(1) and Step A(2) to give alfalfa seeds, the ratio of male sterile hybrid alfalfa plants to male fertile alfalfa plants being in the range of about 1:1 to 3:1, and Step D - non-selectively recovering the seeds from the last-mentioned crossing.

6. The process of claim 5 in which the cross in Step A(2) is
1. between a genic male sterile line of alfalfa plants and a normal line of alfalfa plants, and
2. between a second genic male sterile line of alfalfa plants and a second normal line of alfalfa plants, and the Step C crossing is between the crosses obtained in Step A(1) and those from both A(2) (1) and A(2) (2).

7. A process for producing alfalfa seeds which comprises:

Step A - crossing by controlled pollination,
1. a cytoplasmic male sterile line of alfalfa plants with a maintainer line of alfalfa plants to give cytoplasmic male sterile hybrid alfalfa seeds, and
2. A genic male sterile line of alfalfa plants with a normal line of alfalfa plants to give male fertile hybrid alfalfa seeds, Step B - selectively recovering the hybrid seeds from both the crossings of Step A(1) and Step A(2), Step C - crossing, using random pollination, the hybrid alfalfa plants derived from randomly mixing and planting the seeds produced in Step A(1) and Step A(2) to give alfalfa seeds, and Step D - non-selectively recovering the seeds from the last-mentioned crossing.

8. A process for producing alfalfa seeds which comprises:

Step A - crossing by controlled pollination a number of cytoplasmic male sterile alfalfa plants with
1. a number of maintainer-type alfalfa plants to give male sterile hybrid alfalfa seeds and
2. a number of restorer lines of alfalfa plants to give male fertile hybrid alfalfa seeds, Step B - selectively recovering the hybrid seeds formed from Step A, Step C - crossing, using either controlled pollination or random pollination, the hybrid alfalfa plants derived from the seeds produced in Step A(1) with Step A(2), Step D - crossing, using random pollination, by randomly mixing and planting the hybrid alfalfa plants derived from the seeds produced in Step C, and Step E - non-selectively recovering the seeds from the last-mentioned crossing.

9. A process for producing alfalfa seeds which comprises:

Step A - crossing by controlled pollination
1. a number of cytoplasmic male sterile alfalfa plants with a number of maintainer lines to give male sterile hybrid alfalfa seeds, and
2. a number of genic male sterile alfalfa plants with a number of normal pollen parents to give male fertile hybrid alfalfa seeds, Step B - selectively recovering the hybrid seeds formed with Step A, Step C - crossing, using either controlled pollination or random pollination, the hybrid alfalfa plants derived from the seeds produced in Step A(1) with Step A(2), Step D - crossing, using random pollination, by randomly mixing and planting the hybrid alfalfa plants derived from the seeds produced in Step C, and Step E - non-selectively recovering the seeds from the last-mentioned crossing.

10. A process for producing alfalfa seeds which comprises:

Step A - crossing by controlled pollination cytoplasmic male sterile alfalfa plants with maintainer-type alfalfa plants to give male sterile hybrid alfalfa seeds, Step B - selectively recovering the hybrid seed from the crossing of Step A, Step C - crossing, using random pollination, the hydrid alfalfa plants derived from randomly mixing and planting seeds obtained in Step A and at least one of a locally adapted variety of alfalfa plants to give alfalfa seeds, and Step D - non-selectively recovering the seeds from the last-mentioned crossing.

11. The process of claim 10 in which the Step C crossing is made with male sterile hybrid alfalfa plants and two locally adapted varieties of alfalfa plants.

12. A process for producing alfalfa seeds which comprises:

Step A - crossing by controlled pollination cytoplasmic male sterile alfalfa plants with maintainer-type alfalfa plants to give male sterile hybrid alfalfa seeds, Step B - selectively recovering hybrid seeds from the crossing of Step A, Step C - crossing by controlled pollination the hybrid alfalfa plants derived from seeds produced in Step A with a second maintainer-type alfalfa plant, Step D - selectively recovering the hybrid seeds from the crossing of Step C, Step E - crossing, using random pollination, the hybrid alfalfa plants derived from seeds produced in Step C randomly mixed with at least one of a locally adapted variety of alfalfa plants to give alfalfa seeds, and Step F - non-selectively recovering the seeds from the last-mentioned crossing.

13. A process for producing alfalfa seeds which comprises crossing by random pollination by randomly mixing and planting two different hybrid alfalfa plants in Step E of claim 12 and non-selectively recovering the seeds produced.

14. A process for producing alfalfa seeds which comprises:

Step A - crossing by controlled pollination cytoplasmic male sterile alfalfa plants with maintainer-type alfalfa plants to give male sterile hybrid alfalfa seeds, Step B - selectively recovering the hybrid seeds from the crossing of Step A, Step C - crossing, using random pollination, the hybrid alfalfa plants derived from randomly mixing and planting seeds produced in Step A and seeds from at least one of a locally adapted variety of alfalfa plants to give alfalfa seeds, Step D - non-selectively recovering the seeds from the last-mentioned crossing, Step E - crossing by controlled pollination cytoplasmic male sterile alfalfa plants with maintainer-type alfalfa plants different from those employed in Step A to give male sterile hybrid alfalfa seeds, Step F - selectively recovering the hybrid seeds from the crossing of Step E, Step G - crossing, using random pollination, the hybrid alfalfa plants derived from randomly mixing and planting seeds produced in Step E and seeds from at least one of a locally adapted variety of alfalfa plants to give alfalfa seeds, Step H - non-selectively recovering the seeds from the last-mentioned crossing, Step I - crossing, using random pollination, the hybrid alfalfa plants derived from randomly mixing and planting seeds produced in Steps C and G, and Step J - non-selectively recovering the seeds from the last-mentioned crossing.

15. The process of claim 2 in which the Step A(1) cross is crossed with a second maintainer line and the Step A(2) cross is a cytoplasmic male sterile alfalfa plant crossed with a maintainer line which is then crossed to the restorer line before the Step C crossing is made.

16. A process for producing alfalfa seeds which comprises:

Step A - crossing by controlled pollination cytoplasmic male sterile alfalfa plants with maintainer line alfalfa plants to give cytoplasmic male sterile hybrid alfalfa seeds, Step B - selectively recovering the hybrid seeds produced in Step A, Step C - crossing, by controlled pollination, cytoplasmic male sterile hybrid alfalfa plants derived from seed produced in Step A with a restorer line of alfalfa plants to give male fertile alfalfa seeds, Step D - selectively recovering the male fertile hybrid alfalfa seeds from the last-mentioned crossing, Step E - crossing, using random pollination, cytoplasmic male sterile hybrid alfalfa plants derived from seed produced in the manner described in Step A randomly mixed with the male fertile alfalfa plants derived from the seed produced in Step C, and Step F - non-selectively recovering the seeds from the last-mentioned crossing.

17. A process for producing alfalfa seeds which comprises:

Step A - crossing by controlled pollination
1. cytoplasmic male sterile alfalfa plants with a maintainer line of alfalfa plants to give cytoplasmic male sterile hybrid alfalfa seeds,
2. genic male sterile alfalfa plants with a normal line of alfalfa plants to give fertile hybrid alfalfa seeds, Step B - selectively recovering the hybrid alfalfa seed produced in Steps A(1) and A(2), Step C - crossing, using controlled pollination, alfalfa plants derived from the seed produced in Step A(1) with a second maintainer line of alfalfa plants to give cytoplasmic male sterile hybrid alfalfa seeds, Step D - selectively recovering the hybrid alfalfa seed produced in Step C, Step E - crossing, using random pollination, the cytoplasmic male sterile hybrid alfalfa plants derived from the seed produced in Step C with the fertile hybrid alfalfa plants derived from the seed produced in Step A(2), and Step F - non-selectively recovering the seeds from the last-mentioned crossing.

* * * * *

UNITED STATES PATENT OFFICE
CERTIFICATE OF CORRECTION

PATENT NO. : 4,045,912
DATED : September 6, 1977
INVENTOR(S) : PAUL L.F. SUN

It is certified that error appears in the above—identified patent and that said Letters Patent are hereby corrected as shown below:

Column 1, line 21, delete "located within" (first occurrence).

Column 6, line 65, "Example 15" should be -- Example 5 --

Column 8, line 67 should read "$2(AB_1 \times B_2)^1$ and $(CD_1 \times D_2)$ (Foundation"

Column 10, Table III, in the column headed "Product" for (3) Hybrid, "$F_1 - A_6B_4A_1R_1$" should be -- $F_1 - A_6B_2A_1R_1$ --

Column 14, line 24, "drid" should be -- brid --

Signed and Sealed this

Twenty-ninth Day of November 1977

[SEAL]

Attest:

RUTH C. MASON
Attesting Officer

LUTRELLE F. PARKER
Acting Commissioner of Patents and Trademarks